(12) United States Patent  (10) Patent No.: US 8,167,987 B2
Tipler  (45) Date of Patent: May 1, 2012

(54) METHODS AND SYSTEMS FOR COOLING A CHROMATOGRAPHIC COLUMN

(75) Inventor: Andrew Tipler, Trumbull, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 12/468,314

(22) Filed: May 19, 2009

(65) Prior Publication Data

US 2009/0277245 A1  Nov. 12, 2009

Related U.S. Application Data

(63) Continuation of application No. 11/452,449, filed on Jun. 14, 2006, now Pat. No. 7,534,286.

(60) Provisional application No. 60/595,191, filed on Jun. 14, 2005, provisional application No. 60/595,679, filed on Jul. 27, 2005.

(51) Int. Cl.
*B01D 53/02* (2006.01)

(52) U.S. Cl. ............... 96/101; 96/103; 96/105; 96/106; 95/87; 73/23.36; 73/23.42

(58) Field of Classification Search ............... 95/82, 87; 96/101, 102, 103, 105, 106; 73/23.35, 23.36, 73/23.42; 210/175, 198.2, 656
See application file for complete search history.

(56) References Cited

U.S. PATENT DOCUMENTS

| | | | |
|---|---|---|---|
| 4,869,876 A | 9/1989 | Arfman et al. | |
| 4,994,096 A | 2/1991 | Klein et al. | |
| 5,305,232 A | 4/1994 | Chimowitz et al. | |
| 5,447,556 A | 9/1995 | Pleil et al. | |
| 5,467,635 A | 11/1995 | Nakagawa et al. | |
| 5,545,242 A | 8/1996 | Whitlock et al. | |
| 5,738,707 A | 4/1998 | Colombo et al. | |
| 5,744,029 A | 4/1998 | Li et al. | |
| 5,795,368 A | 8/1998 | Wright et al. | |
| 5,952,556 A | 9/1999 | Shoji | |

(Continued)

FOREIGN PATENT DOCUMENTS

EP  0741867 B1  11/2001

(Continued)

OTHER PUBLICATIONS

Hermann B W et al. "CGC Using a Programmable electronic Pressure Controller" Journal of High Resolution Chromatography, Wiley VCH, Weinheim, DE, vol. 13, No. 5, May 1, 1990 pp. 361-365 (5 pages).

(Continued)

*Primary Examiner* — Robert Clemente
(74) *Attorney, Agent, or Firm* — St. Onge Steward Johnston & Reens, LLC

(57) ABSTRACT

Systems and methods for cooling a chromatographic column is disclosed generally, comprising heating a chromatographic column, supplying fluid into the column via the inlet end of the column at an inlet pressure, decreasing the temperature of the column, thereby causing the fluid in the column to contract, and controlling the fluid in the column such that the rate at which the fluid in the column contracts does not exceed the flow rate of the fluid supplied to the column. In certain embodiments, the rate of change of the volume of the fluid in the column as the column temperature decreases is modeled, and the rate of contraction of the gas in the column is estimated therefrom. In some embodiments, the column temperature and/or inlet pressure are controlled by a programmable chromatographic oven.

21 Claims, 11 Drawing Sheets

U.S. PATENT DOCUMENTS

| | | | |
|---|---|---|---|
| 6,036,747 | A | 3/2000 | Blumberg et al. |
| 6,248,158 | B1 | 6/2001 | Abdel-Rahman et al. |
| 6,289,287 | B1 | 9/2001 | Meng et al. |
| 2005/0016245 | A1 | 1/2005 | Easterbrook et al. |
| 2005/0284209 | A1 | 12/2005 | Tipler et al. |

FOREIGN PATENT DOCUMENTS

| | | |
|---|---|---|
| JP | 2000508781 T | 7/2000 |
| JP | 2002181799 A | 6/2002 |
| JP | 2006023305 A | 1/2006 |
| WO | 9834106 A1 | 8/1998 |

OTHER PUBLICATIONS

International Search Report; PCT/US2006/023474; Oct. 16, 2006; 5 pages.

Wicar Stanislav "Mass Flow Control and Temperature Programming in Gas Chromatography. Part II. Flow Continuity Equation and its Consequences in Programmed-temperature gas Chromatography" Journal of Chromatography, vol. 298, 1984, pp. 373-383 (8 pages).

Wicar; "Journal of Chromatography"; 1984; vol. 298, p. 373-380.

Hermann, et al.; "Journal of High Resolution Chromatography"; 1990; vol. 13, No. 5, p. 361-365.

METHODS AND SYSTEMS FOR COOLING A CHROMATOGRAPHIC COLUMN

CROSS-REFERENCE TO RELATED APPLICATIONS

This application is a continuation of U.S. patent application Ser. No. 11/452,449, filed Jun. 14, 2006, now U.S. Pat. No. 7,534,286, which in turn claims the benefit of, under Title 35, United States Code, Section 119(e), U.S. Provisional Patent Application Ser. No. 60/595,191, filed Jun. 14, 2005, and U.S. Provisional Patent Application Ser. No. 60/595,679, filed Jul. 27, 2005, the contents of each of which are herein incorporated by reference in their entirety.

FIELD OF THE INVENTION

The present invention relates to systems and methods for cooling a chromatographic column by reducing the ingress of detector gases into a chromatographic column as the column is cooled. More specifically, the invention relates to a method of controlling the fluid flowing into the column as the temperature of the column decreases so as to prevent the rate of contraction of the gases in the column from exceeding the flow rate of the fluid.

BACKGROUND OF THE INVENTION

Gas chromatography is essentially a physical method of separation in which constituents of a vapor sample in a carrier gas are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various components of the sample—which differ based upon differences among partition coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

Temperature programming of the chromatographic column is a technique that has become common in some chromatographic analyses. Temperature programming can extend the range of analytes that can be separated during a single analysis, shorten analysis time, improve peak shape, and eliminate and/or reduce unwanted sample residue from the column after the chromatography has finished. At the end of the temperature program, the column oven is cooled back to the program's initial temperature so that it is ready for the next analysis. This cool-down step is a part of the analytical cycle, but it can represent a significant and unproductive portion of the total time needed to perform a sequence of analyses.

It has become fairly common in modern instrumentation to accelerate this cool-down process, which is performed by a chromatographic oven housing the column, so that the gas chromatograph can spend a greater proportion of its time on productive chromatography, thereby increasing the throughput of samples. Such acceleration of the cool-down process can result in significant benefits in terms of time and cost.

Accordingly, some teachings include oven designs that accelerate the cooling rate—in some cases, by a factor in the range of five to ten. However, in some instances, the carrier gas inside the column contracts during this rapid cooling at a rate faster than that at which the carrier gas is entering into the column. It has been discovered that this can produce a partial vacuum at the column outlet. Because the column outlet typically resides inside a detector, this vacuum will draw gases that are inside the detector back into the column during such rapid cooling, and these gases may be hostile to the column. For instance, in the case of a detector where combustion occurs, such as, for example, a flame ionization detector, a flame photometric detector, or a nitrogen-phosphorus detector, undesirable gases such as oxygen and water vapor may be drawn back into the outlet end of the column.

Several methods are available for preventing this ingress of the detector gases into the column during cooling. One such method entails introducing a small flow of a "make-up" gas between the column and the detector. This would ensure that, as the gas in the column contracts, only pure carrier gas would enter the column exit. However, this approach requires the use of an additional carrier gas supply, which is undesirable due to the concomitant extra cost and complexity necessary to install and operate an extra gas supply.

Additionally, some columns generate significant stationary phase bleed when operated at temperatures close to their specified limit. A fast cooling oven can "chill" this bleed, causing it to collect in pockets along the column. The next time the column is temperature programmed, these focused areas of bleed may manifest themselves as 'ghost peaks' on the chromatogram.

SUMMARY OF THE INVENTION

The present teachings include systems and methods for cooling a chromatographic column by controlling the flow of fluid into a chromatographic column during cooldown such that detector gases drawn back into the column are reduced during a decrease of the column temperature. Further, systems and methods are provided for controlling the flow of fluid into a chromatographic column that permit rapid cooling of the column. Additionally, systems and methods are provided for controlling the flow rate of a fluid into a chromatographic column that does not require an additional carrier gas supply. Also, systems and methods are provided for controlling a chromatographic column so as to reduce the effects of stationary phase bleed.

To achieve at least some of the objects listed, the invention comprises a method for cooling a chromatographic column, the chromatographic column having (i) an inlet end, and (ii) an outlet end for communicating fluid to a detector, the method including heating the column to a column temperature, supplying fluid into the column via the inlet end at an inlet pressure, decreasing the column temperature to cause the fluid in the column to contract, and increasing the inlet pressure such that the rate at which the fluid in the column contracts does not exceed the flow rate of the fluid supplied to the column.

In certain embodiments, the step of increasing the inlet pressure includes modeling the rate of change of the volume of the fluid in the column as the column temperature decreases and estimating the rate of contraction of the fluid in the column by differentiating the modeled volume of the fluid. In some of these embodiments, the step of modeling the rate of change of the volume of the fluid includes calculating volume data representing the volume of the fluid in the column at different temperatures, obtaining temperature data representing the rate of decrease in column temperature, and using the volume data and the temperature data to determine the rate of change of the volume of the fluid in the column.

In certain of these embodiments, the volume data is calculated in accordance with the equation $$V_a = \frac{\pi \cdot d_c^2 \cdot L_c \cdot T_a(p_i^3 - p_o^3)}{6 \cdot p_a \cdot T_c \cdot (p_i^2 - p_o^2)}$$

where $V_a$ is the volume of the fluid in the column, $T_c$ is the temperature of the column, $d_c$ is the internal diameter of the column, $L_c$ is the length of the column, $T_a$ is the ambient temperature, $p_a$ is the ambient pressure, $p_i$ is the absolute pressure at the column inlet, and $p_o$ is the absolute pressure at the column outlet.

In certain embodiments, the step of supplying fluid into the column includes introducing the fluid into the column with a chromatographic injector. In some of these embodiments, the step of increasing the inlet pressure includes controlling the pressure with the injector.

In some embodiments, the column temperature is controlled via a chromatographic oven.

In another embodiment, the invention comprises a method for cooling a chromatographic column, the chromatographic column having (i) an inlet end for receiving a carrier gas supplied by a sampling device, and (ii) an outlet end for providing gas to a detector, the method including heating the column to a column temperature, supplying the gas into the column via the inlet end at an inlet pressure, and decreasing the column temperature to cause the gas in the column to contract, and increasing the inlet pressure such that the rate at which the gas in the column contracts does not exceed the flow rate of the gas supplied to the column.

In still another embodiment, the invention comprises a method for cooling a chromatographic column, the method including heating the column to a column temperature, supplying fluid into the column, determining a cooling rate at which the temperature of the column can be decreased, which causes the fluid in the column to contract, such that the rate at which the fluid in the column contracts does not exceed the flow rate of the fluid supplied to the column when the column temperature is decreased at a rate that does not exceed the determined cooling rate, and decreasing the column temperature at a rate that does not exceed the determined cooling rate.

In certain of these embodiments, the step of determining a cooling rate includes determining a maximum cooling rate at which the temperature of the column can be decreased such that the rate at which the fluid in the column contracts does not exceed the flow rate of the fluid supplied to the column, and in some cases, the step of decreasing the column temperature comprises decreasing the column temperature at the maximum cooling rate.

In some embodiments, the step of heating the column causes stationary phase bleed, and the step of decreasing the column temperature includes decreasing the column temperature at a first cooling rate until the column reaches a threshold temperature, and decreasing the column temperature at a second cooling rate that is faster than the first cooling rate, where the threshold temperature comprises a temperature below which substantially no stationary phase bleed occurs.

In certain embodiments, the step of decreasing the column temperature at a rate that does not exceed the determined cooling rate includes receiving a flow of ambient air through a chromatographic oven inlet, and throttling the flow of ambient air.

In yet another embodiment, the invention comprises a system for cooling a chromatographic column, including a chromatographic column for communicating fluid to a detector, the column having an inlet end through which fluid flows into the column and an outlet end through which fluid flows to the detector, a chromatographic oven in which the column is at least partially disposed for heating the column, and a pressure-controlling device located at the inlet end of the column that controls the pressure at which the fluid flows into the column, wherein the oven is temperature-programmable to lower the temperature of the column, whereby the fluid in the column contracts, and wherein the pressure-controlling device controls the pressure at which the fluid flows into the column such that the rate at which the fluid in the column contracts does not exceed the flow rate of the fluid flowing into the column.

In some embodiments, a detector is provided for receiving the fluid from the outlet end of the column.

In certain embodiments, the invention further includes a sampling device for supplying the fluid to the column. In some of these embodiments, the sampling device is a headspace sampler, while in other embodiments, the sampling device is a thermal desorption unit.

DETAILED DESCRIPTION OF THE INVENTION

Figure 1:
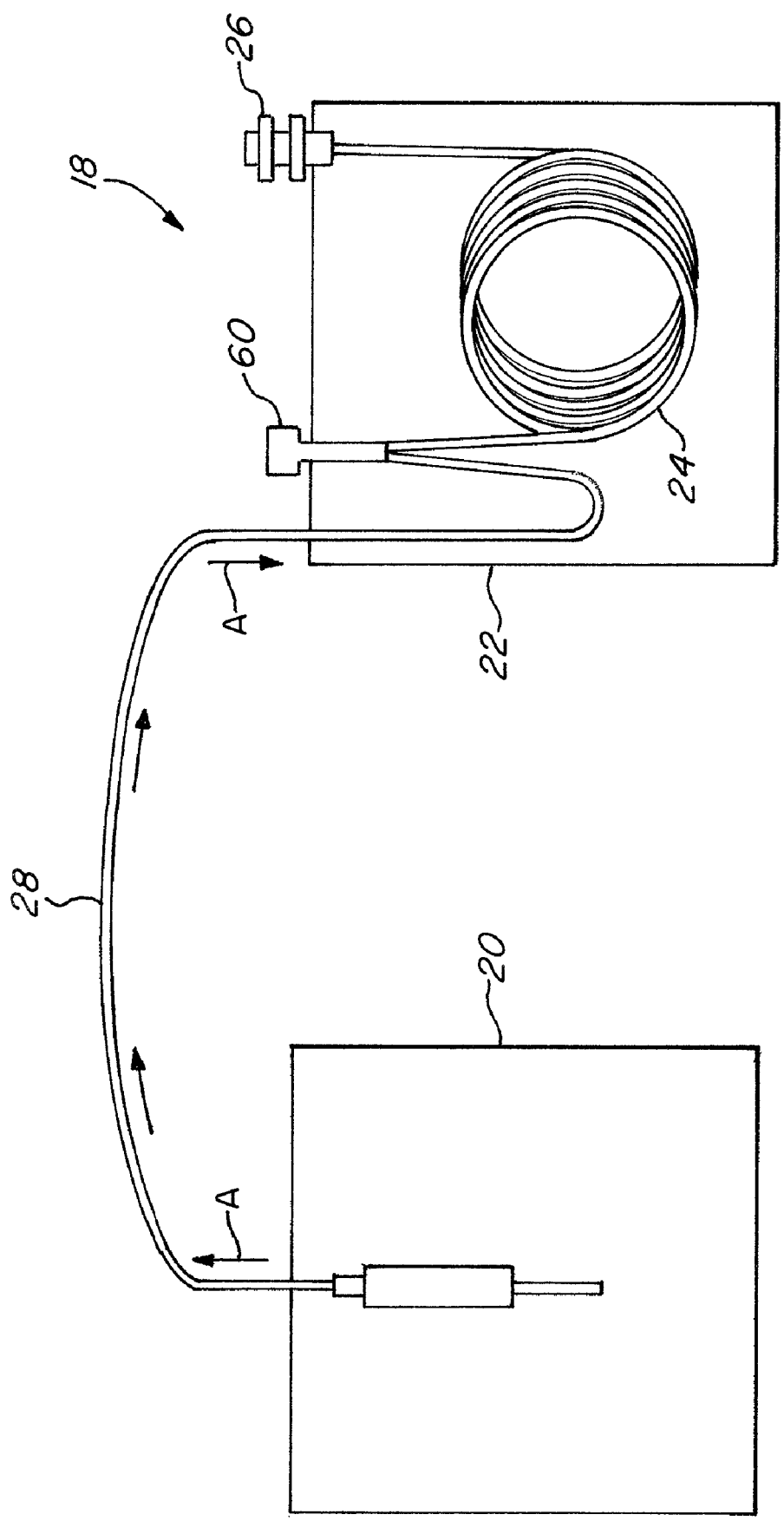
FIG. 1 is a schematic view of sampling system in accordance with one embodiment of the invention.

The basic components of one embodiment of a system for preventing the ingress of detector gases into a chromatographic column in accordance with the invention are illustrated in FIG. 1. As used in the description, the terms "top,"

"bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 18 includes a sampling device 20, such as a thermal desorption unit or a headspace sampler, in which a sample vessel, such as a sorbent tube, is disposed. The system 18 also includes a chromatographic oven 22, which, in certain embodiments, is temperature-programmable. A chromatographic column 24 is at least partially disposed in the oven 22, and the outlet end of the column 24 is connected to a detector 26. The sampling device 20 is connected to the inlet end of the column 24 via a transfer line 28, through which a sample mixture is communicated to the column 24 (indicated by arrows A), which may, for example, comprise a length of fused silica restrictor tubing. Additionally, it should be noted that, while the illustrated embodiment depicts the use of a sampling device 20, the present invention may be employed in many chromatographic applications, and does not necessarily require the use of such a device. Therefore, the present invention may be employed, for example, with a traditional liquid injection (i.e., with a syringe).

A pressure-controlling device 60 is located at the inlet end of the column 24. In some embodiments, the pressure controlling device 60 is an interface device 60 that interfaces the transfer line 28 with the column 24. Such an interface device 60 may comprise a chromatographic injector, such as, for example, the Programmed-Temperature Split/Splitless Inlet System (PSS) Injector manufactured by PerkinElmer Instruments LLC. For instance, a system in which a chromatographic injector interfaces a transfer line with a chromatographic column is described in U.S. Patent Application No. 2005/0284209 by Tipler et al, the contents of which are herein incorporated by reference in their entirety.

The pressure-controlling device controls the pressure at which fluid enters the column 24 via the column inlet, as is further explained below. Though the pressure-controlling device may, as described above, be an interface device for interfacing the sampling device (or transfer line connected to the sampling device) and the chromatographic column, it should be noted that some gas chromatographs are equipped with electronic programmable pneumatic controls, and thus, the chromatograph is able to readily increase the column inlet pressure in order to achieve a desired flow rate through the column. In these cases, the pressure controlling device may simply be part of the chromatographic oven.

Likewise, in some applications, the gas pressure is controlled on a device remote from the chromatograph, such as the sampling device 20. For instance, a system in which a temperature sensor is employed to measure the temperature of the column and communicate this measurement to the sampling device, which then adjusts the pressure at which it supplies the fluid based on this temperature, is disclosed in U.S. Patent Application No. 2006/0016245 by Tipler et al, the contents of which are herein incorporated by reference in their entirety.

The operation of the system depends, in part, upon an adequate prediction of the volume of the gas in the column 24. During use, the chromatographic column 24 will typically have a pressure drop across it, and thus, the internal pressure will be higher at the inlet end than the outlet end of the column, and as a result, the gas will be more compressed at one end than at the other. Accordingly, expressions that account for this effect can be employed to calculate the amount of gas in a particular column.

As is well known, the pressure gradient inside a column can be described in accordance with the following equation:

$$P_z = \sqrt{P^2 - (z/L)(P^2 - 1)} \quad (1)$$

where: $P_z$ is the pressure ratio ($p_z/p_o$)
P is the pressure ratio ($p_i/p_o$)
$p_z$ is the pressure at point z
$p_i$ is the pressure at the column inlet
$p_o$ is the pressure at the column outlet
z is the distance from the inlet to the point being measured
$L_c$ is the length of the column Accordingly, Equation 1 can be rearranged as follows:

$$p_z = \sqrt{p_i^2 - (z/L)(p_i^2 - p_o^2)} \quad (2)$$

From the pressure gradient, the density at each point in the column can be calculated and, hence, the total amount of carrier gas in the column can likewise be calculated.

The molar density δ of the gas is represented as:

$$\delta \frac{n}{V} \quad (3)$$

where: n is the number of moles
V is the volume

Equation 3 can be combined with the Ideal Gas Law, which is represented as:

$$p \cdot V = n \cdot R \cdot T \quad (4)$$

where: p is the pressure
R is the gas constant (0.0821 L atm mol$^{-1}$ K$^{-1}$)
T is the temperature This combination of Equations 3 and 4 provides the following expression for the gas density δ for a given point z in the column:

$$\delta = \frac{p_z}{R \cdot T_c} \quad (5)$$

By substituting the value for the pressure $p_z$ for a point z from Equation 2 into Equation 5, the following expression for the gas density is derived:

$$\delta_x = \frac{1}{R \cdot T_c} \sqrt{p_i^2 - x(p_i^2 - p_o^2)} \quad (6)$$

where: x is the column fraction (z/L)

The amount of gas within a length of the column is then calculated by multiplying the volume within that length by the integral of the density across that length, as shown in the following equation:

$$n_x = \frac{\pi \cdot d_c^2 \cdot z}{4} \int_0^{\frac{z}{L}} \frac{1}{R \cdot T_c} \sqrt{p_i^2 - x(p_i^2 - p_o^2)} \cdot dx \quad (7)$$

where: $n_x$ is the number of moles of gas in the column up to point x

Integrating Equation 7, setting z=L (for the whole column) and further reducing the equation results in the following:

$$n_x = \frac{\pi \cdot d_c^2 \cdot z}{4} \frac{1}{R \cdot T_c} \frac{2}{3(p_i^2 - p_o^2)} \left[ (p_i^2 - x(p_i^2 - p_o^2))^{\frac{3}{2}} \right]_{x=0}^{x=\frac{z}{L}} \quad (8)$$

$$n_x = \frac{\pi \cdot d_c^2 \cdot L}{4} \frac{1}{R \cdot T_c} \frac{2}{3} \frac{(p_i^3 - p_o^3)}{(p_i^2 - p_o^2)} \quad (9)$$

$$n_x = \frac{\pi \cdot d_c^2 \cdot L}{6 \cdot R \cdot T_c} \frac{(p_i^3 - p_o^3)}{(p_i^2 - p_o^2)} \quad (10)$$

By applying the Ideal Gas Law (Equation 4) to Equation 10, the amount of gas in the column can be expressed as the equivalent volume it would occupy under ambient conditions $V_a$ as follows:

$$V_a = \frac{\pi \cdot d_c^2 \cdot L \cdot T_a (p_i^3 - p_o^3)}{6 \cdot p_a \cdot T_c \cdot (p_i^2 - p_o^2)} \quad (11)$$

where: $T_a$ is the ambient temperature
$p_a$ is the ambient pressure

Figure 2:
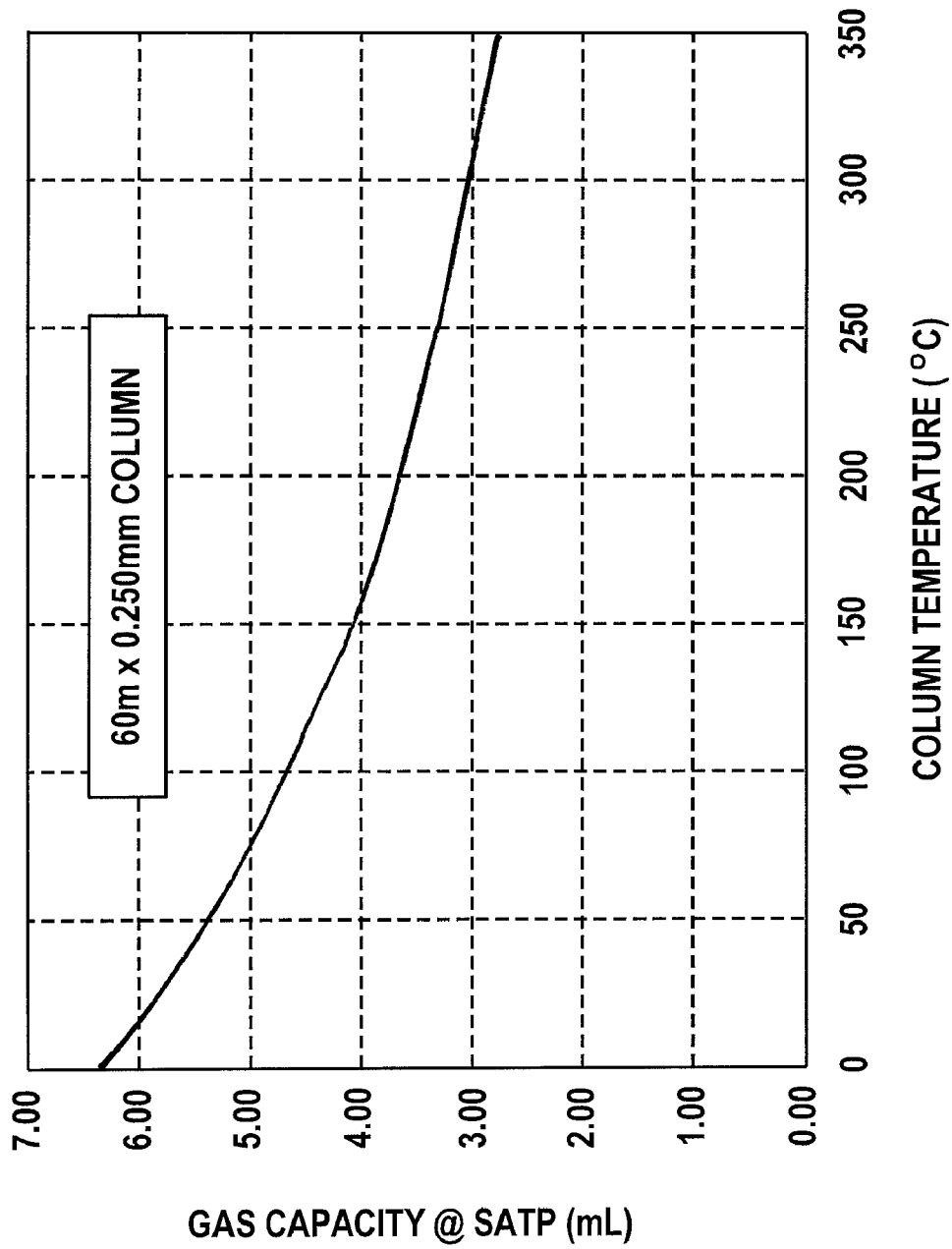
FIG. 2 is a graph plotting the effective volume of gas in a column described in Table 1.

Using Equation 11, the amount of gas in the column can be calculated over a range of applied temperatures for particular column geometries and inlet/outlet pressures. For example, applying Equation 11 to the column described in Table 1 below provides a prediction of the effective volume of carrier gas within this column over a range of temperatures as shown in FIG. 2.

TABLE 1

| | |
|---|---|
| Chromatograph | Prototype GC with fast cooling oven |
| Column | 60 m × 0.250 mm × 1.0 μm PE-5 |
| Oven Temperature | variable |
| Injector | PSS at 375° C. |
| Carrier Gas | Helium at 24 psig |
| Split Flow | 100 mL/min |
| Detector | FID at 400° C. Air 450 mL/min H2 45 mL/min. Range ×1. Attn ×64 |
| Data Collection | TotalChrom 941 Analog Box. 1-Volt input. 5 Hz sampling rate |
| Sample Injected | None |

Figure 3:
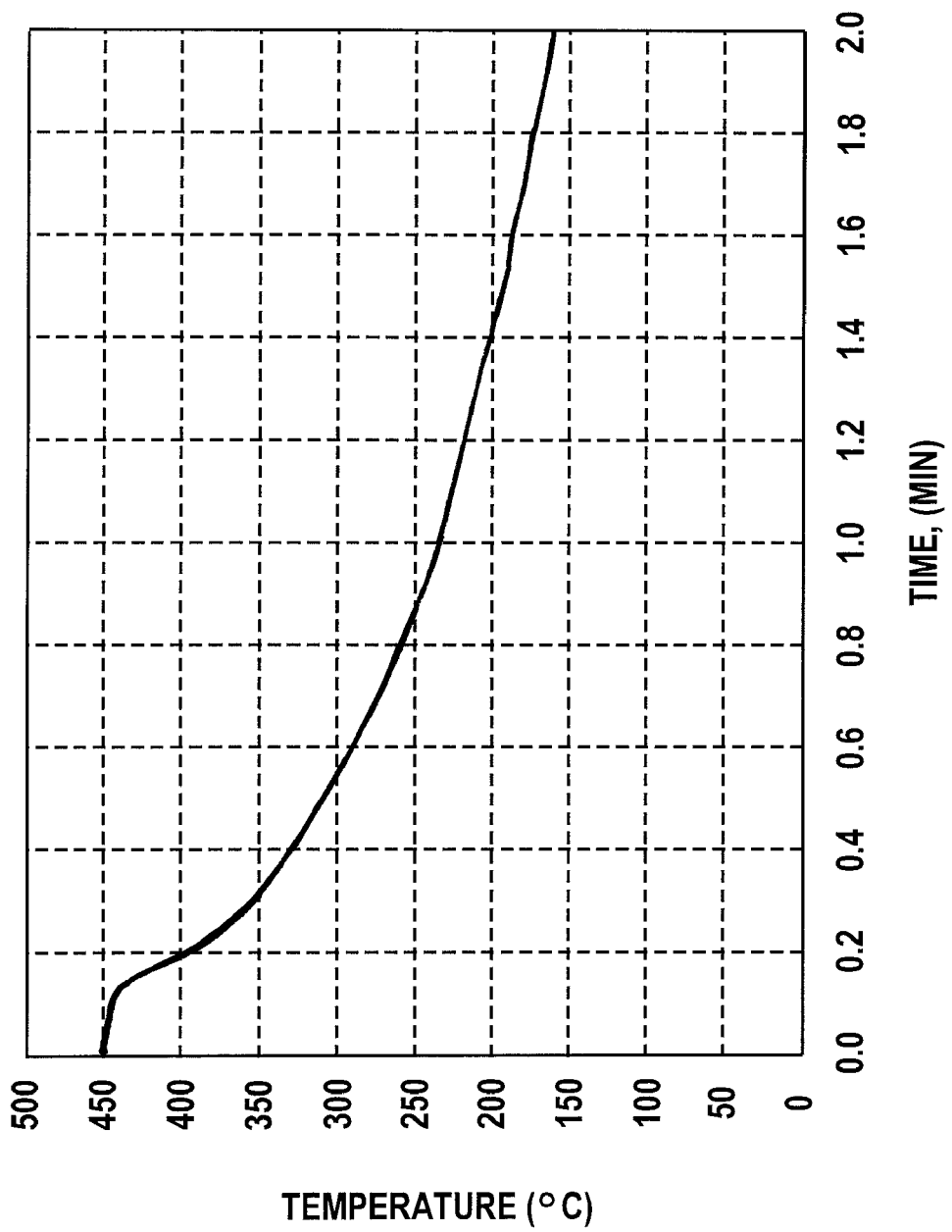
FIG. 3 is a graph illustrating the cooling profile of a chromatographic oven cooled at a traditional rate.
Figure 4:
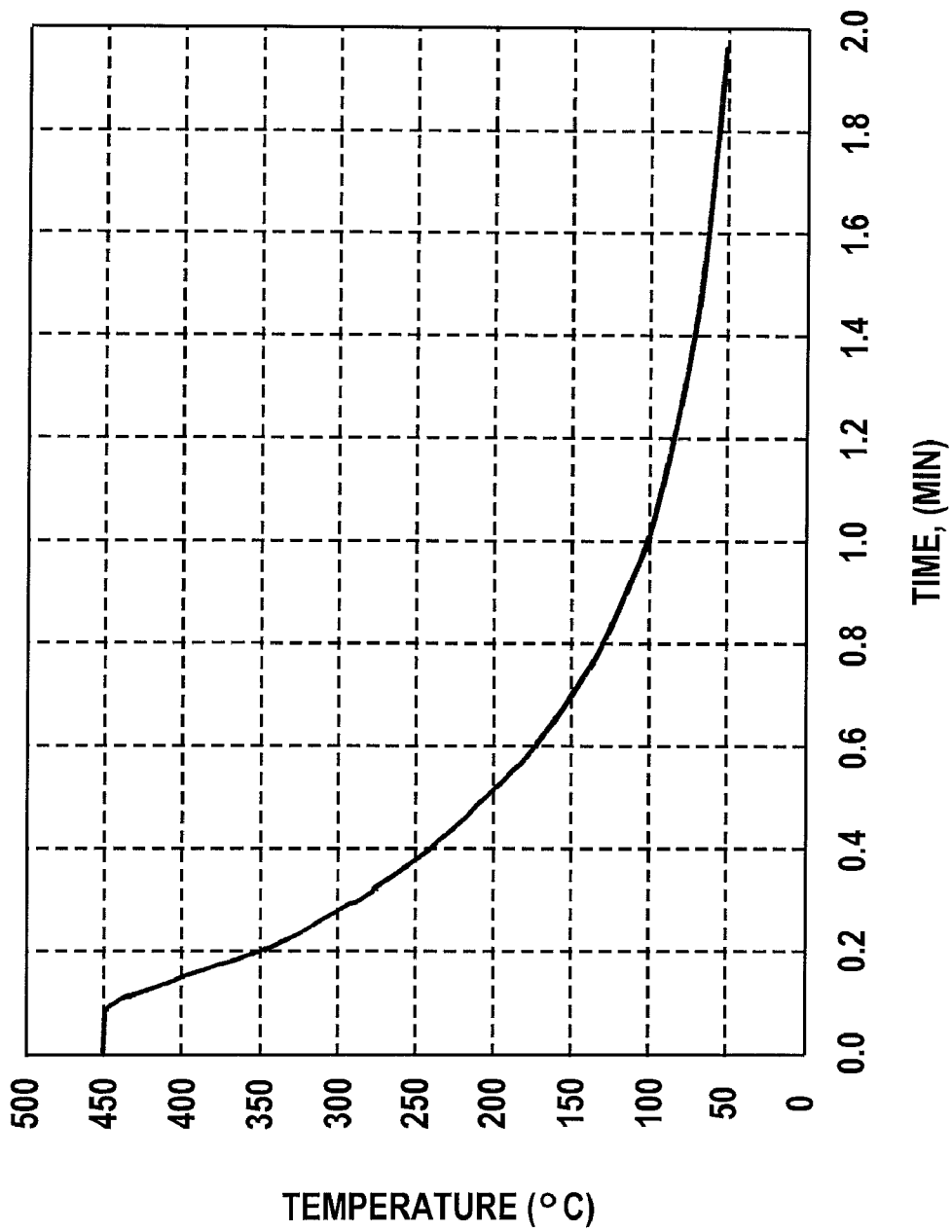
FIG. 4 is a graph illustrating the cooling profile of a chromatographic oven cooled at a more rapid rate than that shown in FIG. 3.

FIGS. 3 and 4 illustrate the cooling profiles of a chromatographic oven cooled at traditional and rapid rates, respectively. The cooling rates shown in FIGS. 3-4 can be applied to the calculations of gas volume that are plotted as a function of temperature in FIG. 2 in order to model the change of the effective volume of gas in the column in the traditional and rapid cooling ovens, as shown in FIGS. 5 and 6, respectively.

Figure 5:
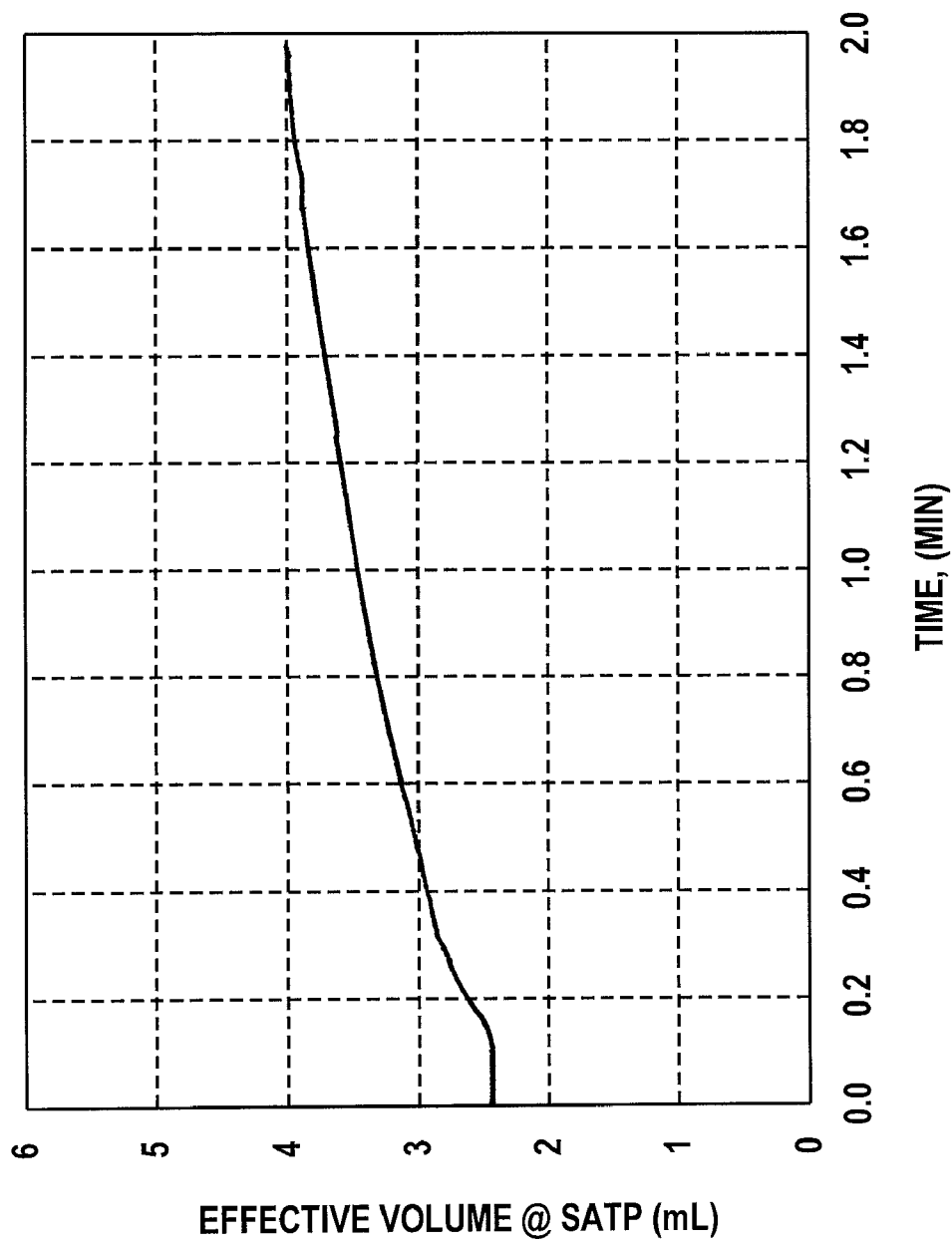
FIG. 5 is a graph illustrating the predicted effective volume of gas in a column described in Table 1 for the cooling rate illustrated in FIG. 3.
Figure 6:
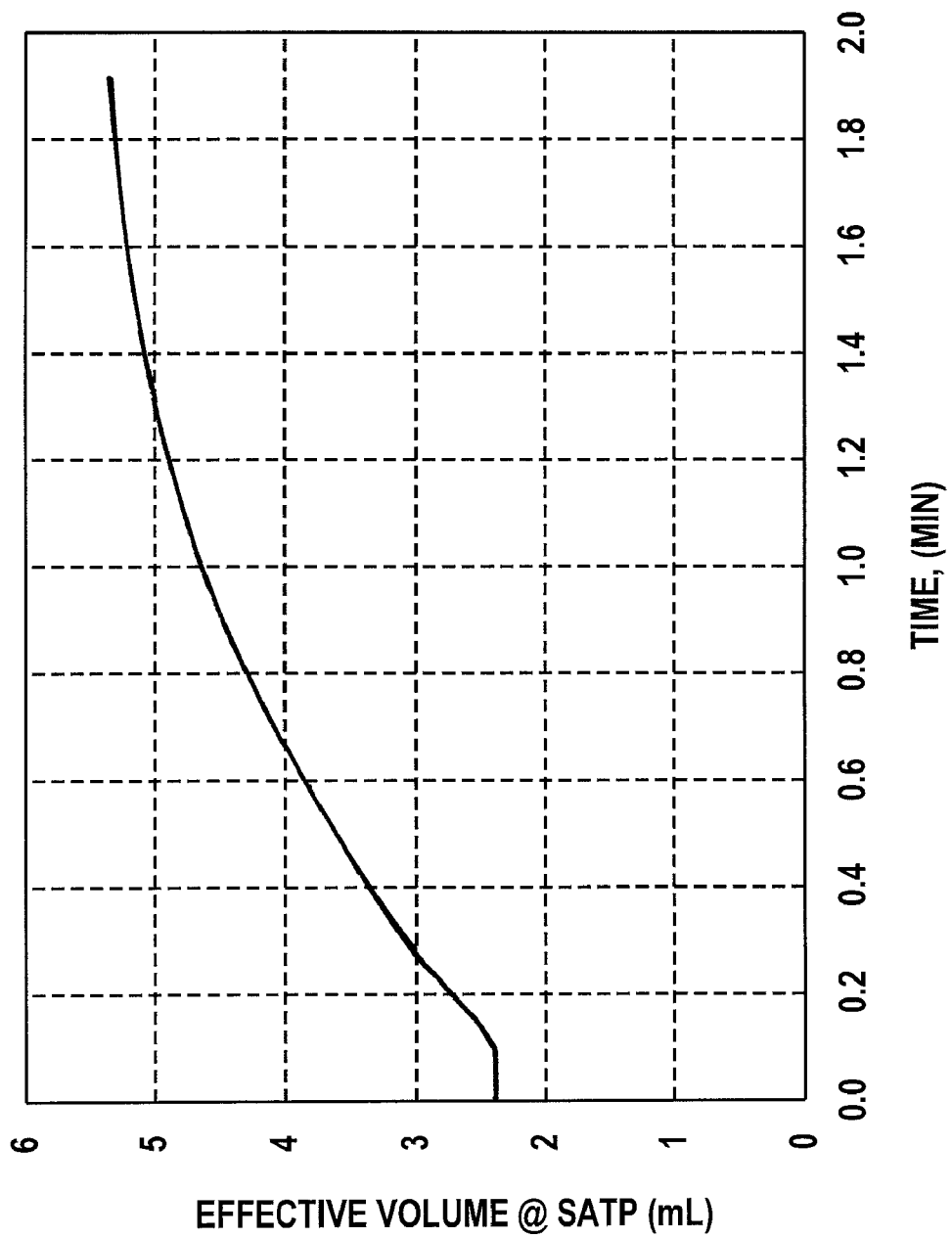
FIG. 6 is a graph illustrating the predicted effective volume of gas in a column described in Table 1 for the cooling rate illustrated in FIG. 4.
Figure 7:
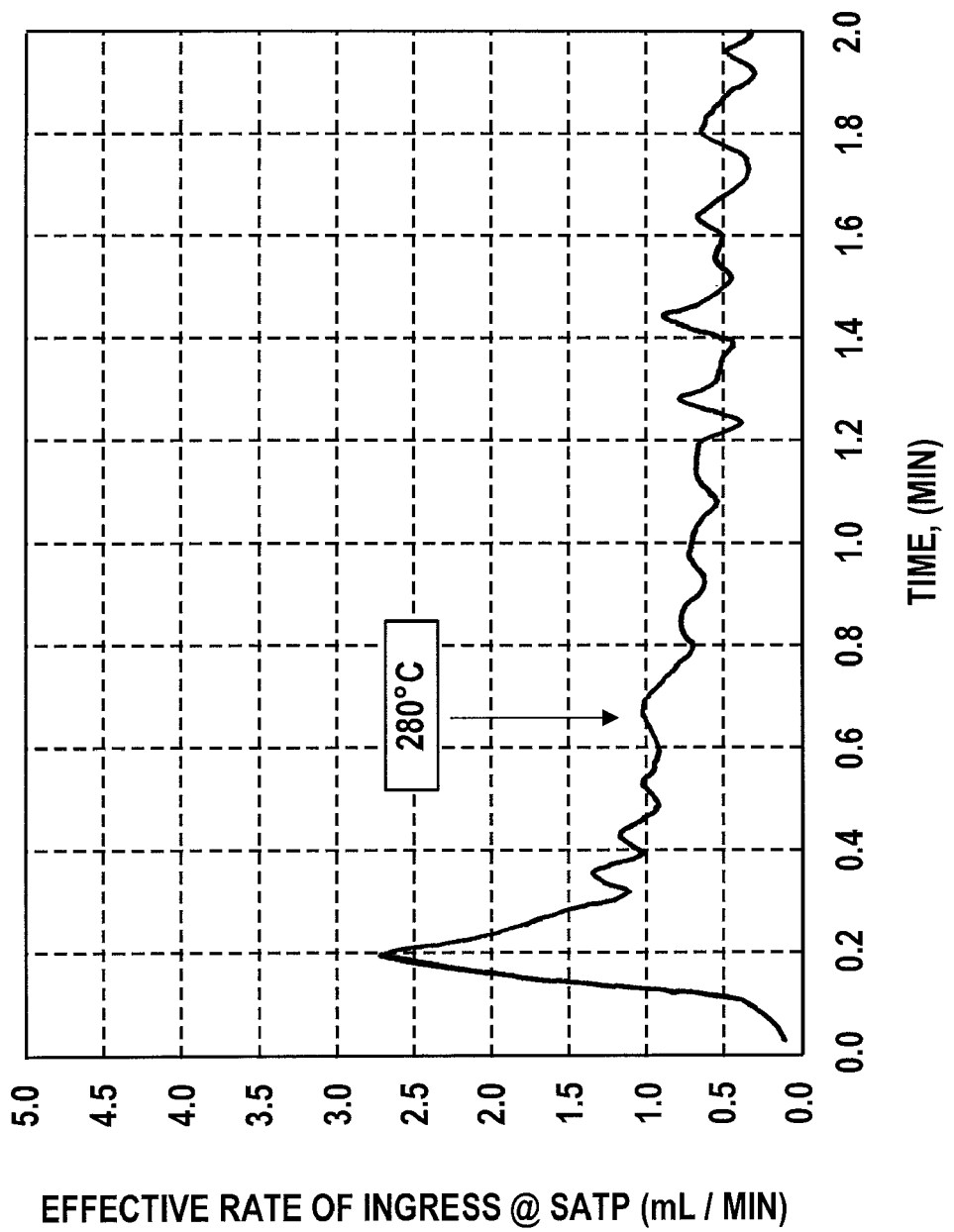
FIG. 7 is a graph illustrating the predicted effective rate of ingress of detector gases into a column described in Table 1 for the cooling rate illustrated in FIG. 3.
Figure 8:
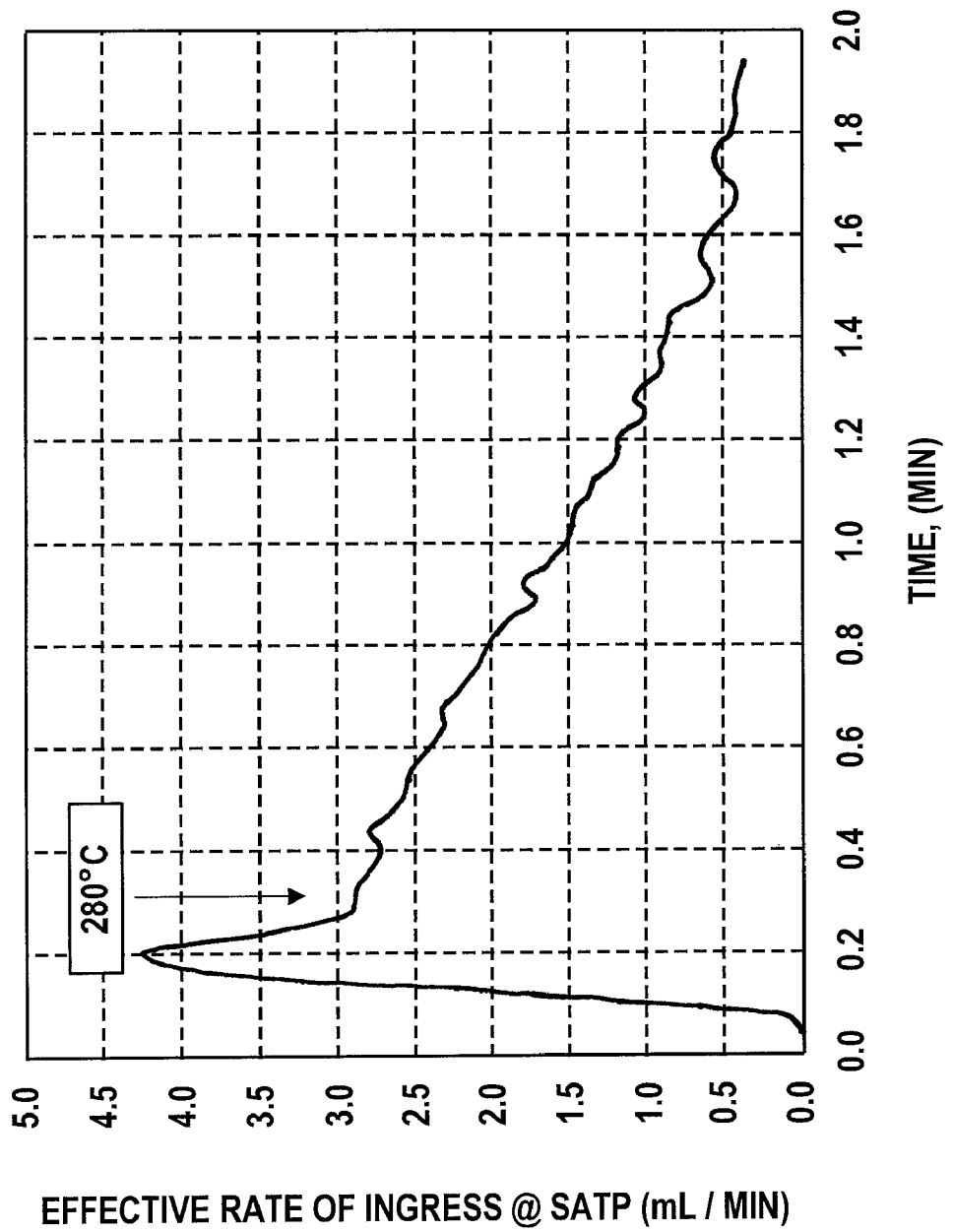
FIG. 8 is a graph illustrating the predicted effective rate of ingress of detector gases into a column described in Table 1 for the cooling rate illustrated in FIG. 4.

The effective rate of contraction of the gas in the column as the temperature of the column decreases can then be predicted by differentiating the traces given in FIGS. 5 and 6, which is shown in FIGS. 7 and 8. These figures illustrate the high level of contraction of the gas that occurs during rapid cooling, leading to undesirable ingress of detector gases.

Normally, the flow of carrier gas through this particular column would be in the range of 0.5 to 1.0 mL/min. As the temperature of the column decreases during cool-down, the gas in the column contracts, causing the pressure to drop at both the inlet and outlet ends of the column. As a result, gas will be drawn into the column from both ends. Approximately an equal amount will be drawn into the column from each end. Therefore, if the gas contacts at a rate of 2 mL/min, it can be assumed that approximately 1 mL/min of gas will be drawn into each end of the column, which is in addition to the normal flow rate of gas flowing through the column as a result of the pressure drop across it.

Referring to FIG. 7, which illustrates the rate of contraction for a traditionally-cooled column, the rate of contraction of the gas is less than 1 mL/min for most of the cooling cycle. This results in a potential ingress of 0.5 mL/min at the outlet end of the column, where the detector gases reside. However, because the normal gas flow through the column is greater than this rate of contraction, no ingress of the detector gases occurs during most of the cycle. However, the rate of contraction can be significant in the beginning of the cooling cycle when cooling from temperatures around 350° C. or higher, as illustrated by the large peak in FIG. 7.

FIG. 8 illustrates how the rate of contraction of the gas in the column is even more significant during a rapid cool-down. Here, the rate of contraction is more than 2 mL/min for most of the cooling cycle. Therefore, the rate of contraction at the detector end is greater than 1 mL/min, and thus, is probably greater than the flow rate of the carrier gas through the column. As a result, ingress of the detector gases is likely to occur for a significant portion of the cool-down process.

By predicting the rate of contraction of the gas over a range of temperatures as described above, it can be determined when the flow through the column 24 must be increased in order to ensure that the rate of contraction does not exceed the flow rate. The pressure-controlling device 60 can thus be used to increase the gas pressure at the column inlet prior to and during the cool-down, thereby preventing ingress of undesirable gases.

Figure 9:
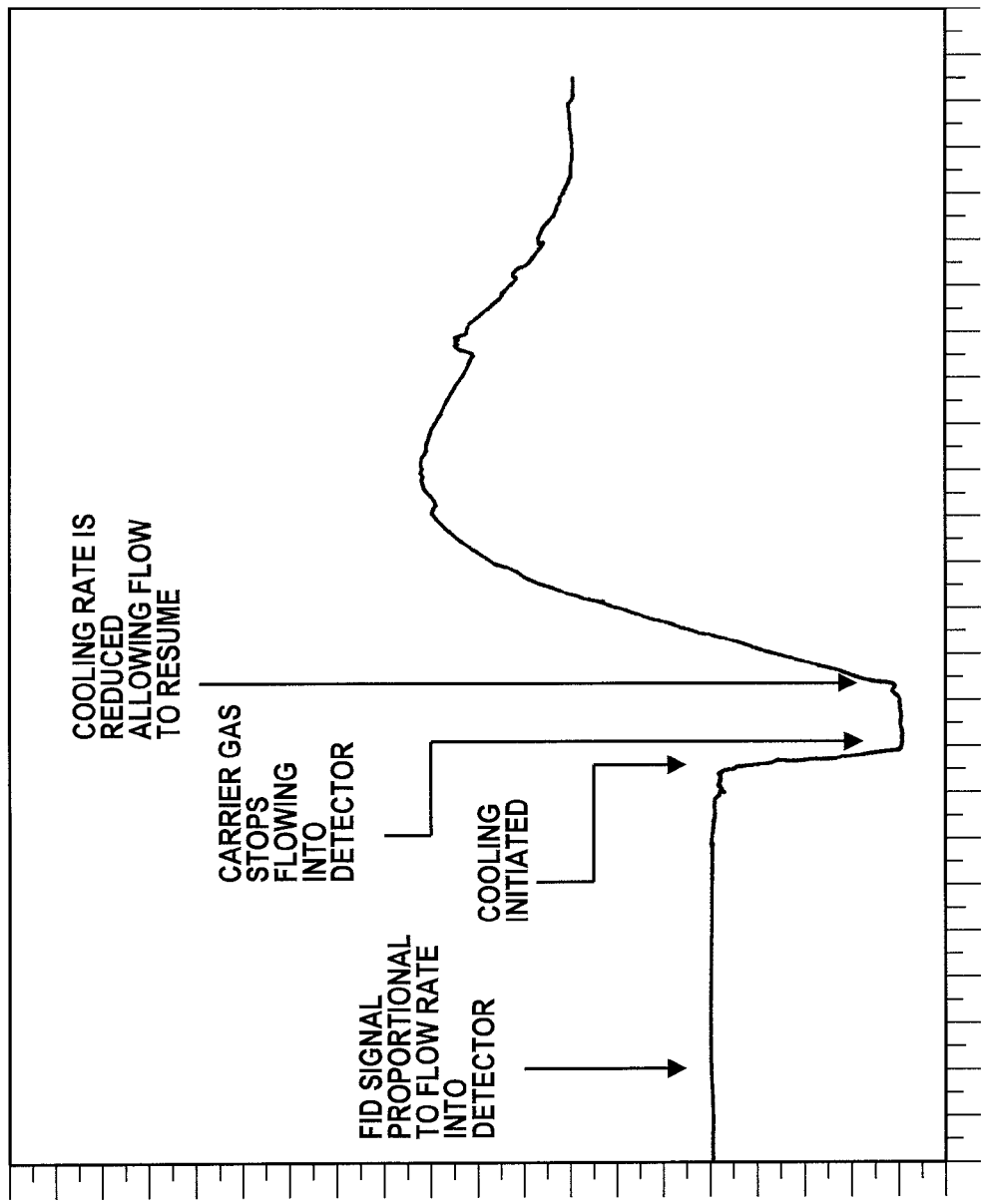
FIG. 9 is a graph illustrating the relative change in flow of carrier gas eluting from a column described in Table 1 for the cooling rate illustrated in FIG. 4 with a constant inlet pressure.
Figure 10:
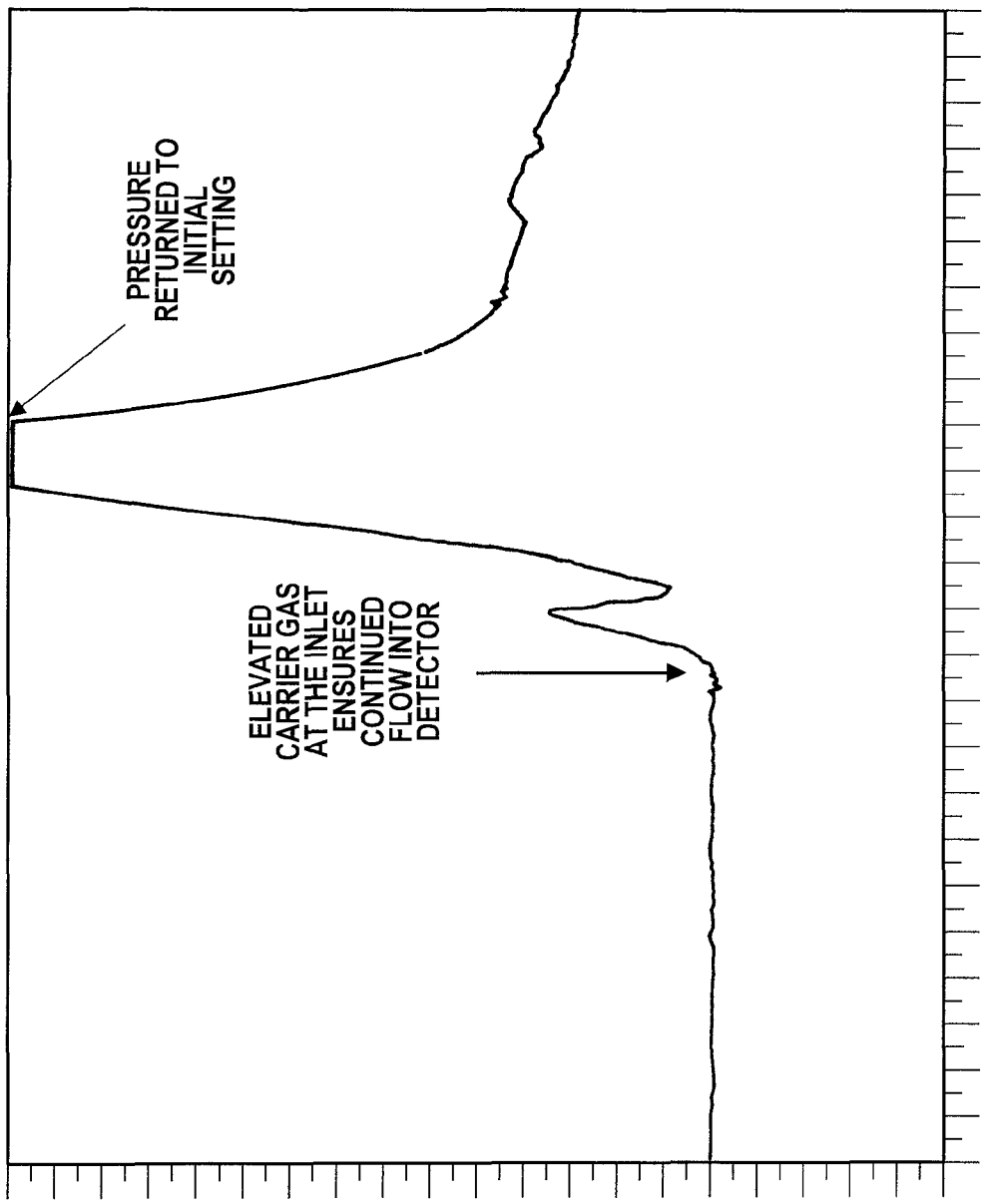
FIG. 10 is a graph illustrating the relative change in flow of carrier gas eluting from a column described in Table 1 for the cooling rate illustrated in FIG. 4 where the column inlet pressure is raised to 50 psig just before and during cooling.

FIGS. 9 and 10 show the change in flow of the gas eluting from the column at a constant applied pressure (FIG. 9) and with an inlet pressure that is increased in accordance with the invention (FIG. 10). As illustrated in FIG. 10, by elevating the carrier gas pressure at the column inlet during the column cool-down in this way, one is able to ensure that the flow rate through the column is increased such that no back-flow occurs at the column outlet.

Figure 11:
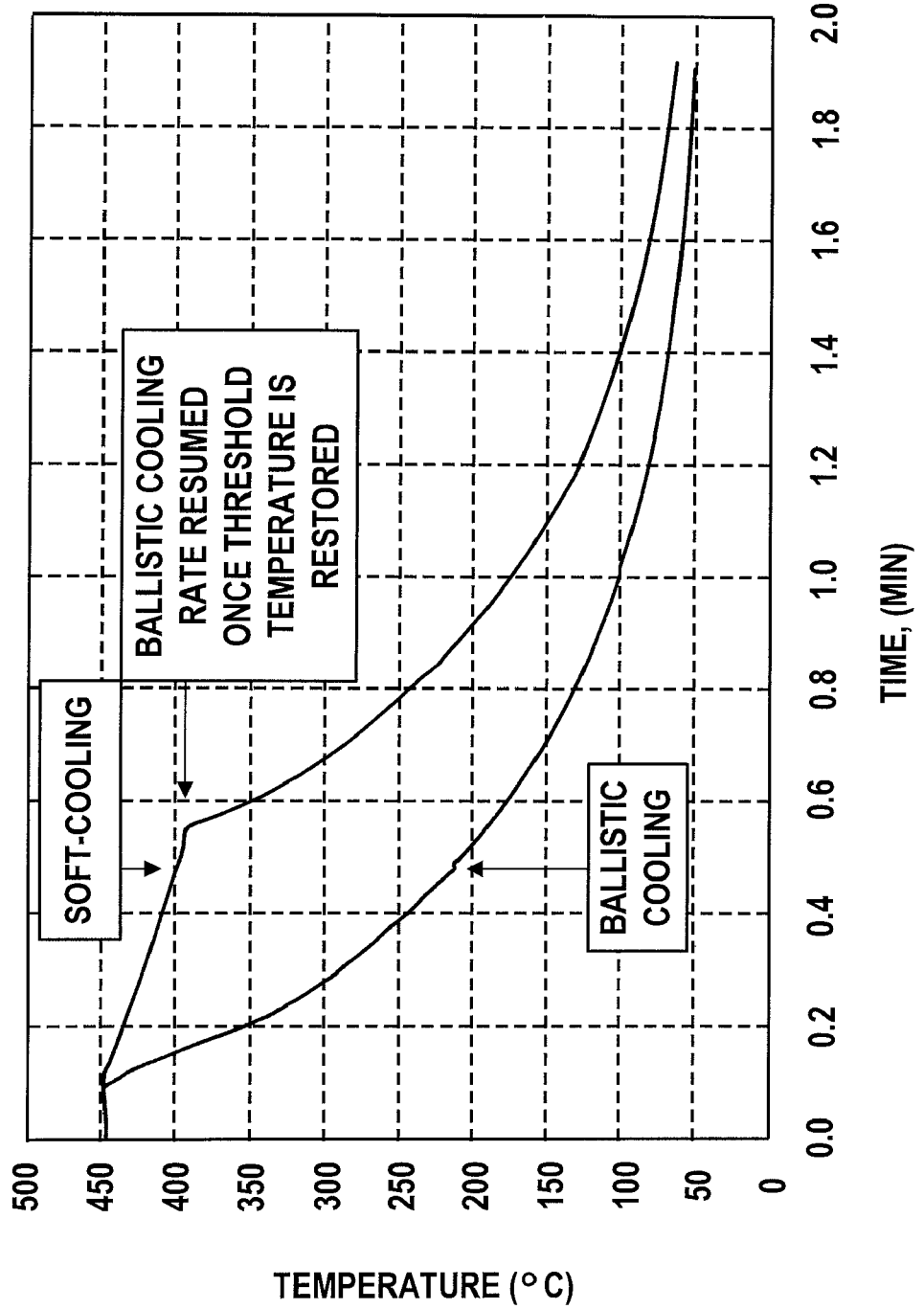
FIG. 11 is a graph illustrating a comparison between completely ballistic cooling and the use of soft cooling.

FIG. 11 illustrates how the relative flow and contraction of the fluid can be controlled without actively adjusting the inlet pressure of the column. Specifically, these relative rates can be manipulated through the use of soft (i.e., less rapid) cooling early in the cool-down process. While the column is cooling, carrier gas will continue to flow as normal into the inlet from the injection system. By reducing the cooling rate, a point is reached where the rate of contraction of the gas within the column is going to be less than the flow rate of the gas flowing through it. Accordingly, the oven is programmed to determine a maximum cooling rate permissible such that the rate of contraction does not exceed the flow rate of the fluid. The oven then throttles the ambient air intake during the beginning of the cooling cycle to keep the flow of air from exceeding this cooling rate. By limiting the cooling rate in this way, one is likewise able to ensure that the flow rate through the column is increased such that no back-flow occurs at the column outlet.

During ballistic cooling of the chromatographic oven, significant cooling rates typically occur at the beginning of the cooling cycle—generally, the first thirty seconds or so. After this initial portion of the cool-down process, the cooling rate tends to decrease as the column gets cooler, and thus, the risk of ingress and possible resultant damage are significantly reduced. Therefore, the algorithm controlling the cooling rate (i.e., limiting the speed with which the column temperature decreases) will typically only affect the initial cooling rate, and thus, the effect on the total time required to complete the cool-down process is minimal.

Additionally, problems associated with stationary phase bleed can also be ameliorated by proper control of the cooling rate. For example, in some embodiments, the system maintains a slow cooling rate until it reaches a certain threshold temperature, which is the point at which substantially no stationary phase bleed occurs. After reaching this threshold temperature, the chromatographic oven will initiate ballistic cooling, thereby minimizing the amount of time the system spends in non-rapid cool-down.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for cooling a chromatographic column, comprising:
   a chromatographic column for communicating fluid to a detector, said column having an inlet end through which fluid flows into said column and an outlet end through which fluid flows to the detector;
   a chromatographic oven in which said column is at least partially disposed that decreases the temperature of said column, thereby causing fluid in said column to contract, said chromatographic oven having programmable pneumatic controls;
   a sampling device for supplying the fluid to said column;
   a transfer line connecting the inlet end of the chromatographic column to the sampling device, through which the fluid is supplied to said column; and
   a pressure-controlling device comprising:
      an interface device that interfaces the transfer line with the chromatographic column, and
      electronic programmable pneumatic controls that controls the interface device, the electronic programmable pneumatic controls being able to control the interface device so that the interface device controls the pressure of fluid entering the column,
      wherein the pressure-controlling device is located at the inlet end of said column and wherein the pressure-controlling device increases the pressure at which the fluid flows into said column as the temperature of the column decreases such that the rate at which the fluid in the column contracts as the temperature of said column decreases does not exceed the flow rate of the fluid flowing into said column.

2. The system of claim 1, wherein said pressure controlling device comprises a chromatographic injector.

3. The system of claim 1, further comprising a detector for receiving the fluid from the outlet end of said column.

4. The system of claim 1, wherein said sampling device comprises a headspace sampler.

5. The system of claim 1, wherein said sampling device comprises a thermal desorption unit.

6. The system of claim 1, wherein the rate at which the fluid in the column contracts is estimated by modeling the rate of change of the volume of the fluid in the column as the column temperature decreases and differentiating the modeled volume of the fluid.

7. The system of claim 6, wherein the rate of change of the volume of the fluid is modeled by calculating volume data representing the volume of the fluid in the column at different temperatures, obtaining temperature data representing a rate of decrease in the temperature of the column, and using the volume data and the temperature data to determine the rate of change of the volume of the fluid in the column.

8. The system of claim 7, wherein the volume data is calculated in accordance with the equation $$V_a = \frac{\pi \cdot d_c^2 \cdot L_c \cdot T_a(p_i^3 - p_o^3)}{6 \cdot p_a \cdot T_c \cdot (p_i^2 - p_o^2)}$$

where $V_a$ is the volume of the fluid in the column, $T_c$ is the temperature of the column, $d_c$ is the internal diameter of the column, $L_c$ is the length of the column, $T_a$ is the ambient temperature, $p_a$ is the ambient pressure, $p_i$ is the absolute pressure at the column inlet, and $p_o$ is the absolute pressure at the column outlet.

9. The system of claim 1, wherein the pressure controlling device is part of said chromatographic oven.

10. The system of claim 1, wherein the pressure-controlling device is used to increase the gas pressure at the inlet prior to and during cool down.

11. The system of claim 1, wherein the oven is programmed to determine a maximum cooling rate such that the rate of contraction does not exceed the flow rate of the fluid by throttling the ambient air.

12. A system for cooling a chromatographic column, comprising:
   a headspace sampler for supplying fluid containing analytes to be measured;
   a chromatographic column for receiving the fluid containing the analytes to be measured and communicating the fluid to a detector, said column having an inlet end through which fluid flows into said column and an outlet end through which fluid flows to the detector;
   a chromatographic oven in which said column is at least partially disposed that decreases the temperature of said column, thereby causing fluid in said column to contract;
   a transfer line connecting the inlet end of the chromatographic column to the headspace sampler; and
   a pressure-controlling device comprising:
      an interface device that interfaces the transfer line with the chromatographic column, and
      electronic programmable pneumatic controls that controls the interface device, the electronic programmable pneumatic controls being able to control the interface device so that the interface device controls the pressure of fluid entering the column,
      wherein the pressure-controlling device is located at the inlet end of said column and wherein the pressure-controlling device is located at the inlet end of said column that increases the pressure at which the fluid flows into said column as the temperature of the column decreases such that the rate at which the fluid in the column contracts as the temperature of said column decreases does not exceed the flow rate of the fluid flowing into said column.

13. The system of claim 12, wherein said oven includes programmable pneumatic controls.

14. The system of claim 12, wherein said pressure controlling device comprises a chromatographic injector.

15. The system of claim 12, further comprising a detector for receiving the fluid from the outlet end of said column.

16. The system of claim 12, wherein the rate at which the fluid in the column contracts is estimated by modeling the rate of change of the volume of the fluid in the column as the column temperature decreases and differentiating the modeled volume of the fluid.

17. The system of claim 16, wherein the rate of change of the volume of the fluid is modeled by calculating volume data representing the volume of the fluid in the column at different temperatures, obtaining temperature data representing a rate of decrease in the temperature of the column, and using the volume data and the temperature data to determine the rate of change of the volume of the fluid in the column.

18. The system of claim 17, wherein the volume data is calculated in accordance with the equation $$V_a = \frac{\pi \cdot d_c^2 \cdot L_c \cdot T_a (p_i^3 - p_o^3)}{6 \cdot p_a \cdot T_c \cdot (p_i^2 - p_o^2)}$$

where $V_a$ is the volume of the fluid in the column, $T_c$ is the temperature of the column, $d_c$ is the internal diameter of the column, $L_c$ is the length of the column, $T_a$ is the ambient temperature, $p_a$ is the ambient pressure, $p_i$ is the absolute pressure at the column inlet, and $p_o$ is the absolute pressure at the column outlet.

19. A system for cooling a chromatographic column, comprising:
- a thermal desorption unit for supplying fluid containing analytes to be measured;
- a chromatographic column for receiving the fluid containing the analytes to be measured and communicating the fluid to a detector, said column having an inlet end through which fluid flows into said column and an outlet end through which fluid flows to the detector;
- a chromatographic oven in which said column is at least partially disposed that decreases the temperature of said column, thereby causing fluid in said column to contract;
- a transfer line connecting the inlet end of the chromatographic column to the thermal desorption unit; and
- a pressure-controlling device comprising:
  - an interface device that interfaces the transfer line with the chromatographic column, and
  - electronic programmable pneumatic controls that controls the interface device, the electronic programmable pneumatic controls being able to control the interface device so that the interface device controls the pressure of fluid entering the column,
  - wherein the pressure-controlling device is located at the inlet end of said column and wherein the pressure-controlling device is located at the inlet end of said column that increases the pressure at which the fluid flows into said column as the temperature of the column decreases such that the rate at which the fluid in the column contracts as the temperature of said column decreases does not exceed the flow rate of the fluid flowing into said column.

20. The system of claim 19, wherein said oven includes programmable pneumatic controls.

21. The system of claim 19, wherein said pressure controlling device comprises a chromatographic injector.

* * * * *